US005988027A

United States Patent [19]
Lenox

[11] Patent Number: 5,988,027
[45] Date of Patent: Nov. 23, 1999

[54] SURGICAL ROD CUTTER

[75] Inventor: Linda Kathleen Lenox, Boulder, Colo.

[73] Assignee: Lenox - MacLaren, Boulder, Colo.

[21] Appl. No.: 08/856,135

[22] Filed: May 14, 1997

[51] Int. Cl.$^6$ .................................................. B26D 3/16
[52] U.S. Cl. .................................. 83/13; 83/200; 83/634; 83/699.61
[58] Field of Search .................................. 16/115; 83/13, 83/199, 200, 633, 634, 694, 699.61; 30/93, 94, 95, 341, 340, 193, 186, 175

[56] References Cited

U.S. PATENT DOCUMENTS

| | | | |
|---|---|---|---|
| 78,420 | 6/1868 | Bryan | 83/633 |
| 132,544 | 10/1872 | Snow | 83/694 X |
| 368,470 | 8/1887 | Hammond | 30/193 |
| 596,837 | 1/1898 | Werner | 83/199 |
| 975,112 | 11/1910 | Bilcsik | 83/199 |
| 1,265,345 | 5/1918 | La Rock | 83/200 |
| 1,729,264 | 9/1929 | Fitch | 30/193 X |
| 2,057,201 | 10/1936 | McCluskey | 30/341 X |
| 2,168,121 | 8/1939 | French | 15/144.3 |
| 2,239,852 | 4/1941 | Lind | 30/193 |
| 2,348,903 | 5/1944 | Hart | 30/341 X |
| 3,220,294 | 11/1965 | Bradburn, Sr. | 83/633 |
| 3,669,463 | 6/1972 | Boudreau | 16/115 X |
| 4,048,735 | 9/1977 | Brunty | 37/130 |
| 5,060,382 | 10/1991 | Wilhelm et al. | 30/341 X |
| 5,156,074 | 10/1992 | De Ros et al. | 83/633 |
| 5,172,622 | 12/1992 | Sabin | 83/633 |
| 5,261,303 | 11/1993 | Strippgen | 63/199 |
| 5,285,702 | 2/1994 | Hillinger | 16/115 |
| 5,404,616 | 4/1995 | Carmien | 30/341 X |
| 5,493,758 | 2/1996 | Carmien | 16/115 |
| 5,515,574 | 5/1996 | Larson | 16/115 |

FOREIGN PATENT DOCUMENTS

| | | | |
|---|---|---|---|
| 431112 | 12/1924 | Germany | 83/633 X |
| 102802 | 1/1994 | Switzerland | 83/200 |
| 570155 | 6/1945 | United Kingdom | 30/341 |

*Primary Examiner*—Rinaldi I. Rada
*Assistant Examiner*—Charles Goodman
*Attorney, Agent, or Firm*—Sheridan Ross P.C.

[57] ABSTRACT

A manually operated surgical steel rod cutter is disclosed. The rod cutter has a rod shearing tool head for cutting a rod when the rod is provided within aligned bores of two shearing subassemblies of the tool head. To cut the rod, an operator rotates an extendable handle to a substantially vertical position, inserts the rod in the tool head and rotates the handle to a substantially horizontal position. In order to increase the operator's shearing leverage, the handle can be extended from its retracted compact position by a linear pulling motion on a handle grip. The motion causes a handle extension that is adjacent and along the length of a first portion of the handle that has one end attached to the tool head, to extend from a sheath also attached to the first portion. The handle extension subsequently locks into an extended position when fully extended. The handle also has a vertical bow or bend which cooperates with a handle stop so that the handle not only rotates through an angle effective for shearing of rods but also limits handle movement in the horizontal direction so that an operator's hand on the handle grip does not contact the surface upon which the rod cutter rests.

8 Claims, 3 Drawing Sheets

SURGICAL ROD CUTTER

FIELD OF THE INVENTION

The present invention relates to a cutting device for surgical rods and more particularly relates to a rod cutting device that has a telescoping handle elevated above a cutting plane so as to protect a user's hand during operation.

BACKGROUND OF THE INVENTION

In the cutting of metal rod materials, and in particular, toughened surgical steel, superior accuracy is required given that the rod being cut is used inside a patient's body. In the past, bolt cutting devices have been used by surgeons having compound levers and pivoted jaws. The problems encountered with such bolt cutting devices, however, is that the cut ends of rods were often left rough or having a wedge-shaped tip due to the extreme compression of metal during the cutting operation. Bolt cutters also prove to be difficult to use in the operating room due to the possibility that work pieces have been known to be propelled in unpredictable directions during the cutting operation, causing concern for operating personnel, as well as patients. In particular, when a rod is cut in this manner while a portion is in the patient, the force from such a compressed type cut will also be transmitted to the rod section in the patient causing some fracture of the implant placement in the bone. Moreover, given the extreme toughness of surgical metal rods, conventional bolt cutters are often difficult to operate manually and require significant strength of the operator. Numerous rod and bolt cutters have been developed having various designs and that are capable of providing a satisfactory cutting edge of a hardened surgical steel rod. For example, U.S. Pat. No. 5,261,303 to Strippgen describes a rod cutter that operates by a shearing action with applied rotatory torque, shearing surgical metal rods with excellent smoothness on the cut end. A disadvantage with this rod cutter device, however, is that during the final rotary motion of the cutting operation the operator's hand would often come into contact with a table top surface upon which the rod cutter was placed. Moreover, the design incorporates a pivotable handle that folds toward the cutting assembly in a manner wherein the hand grip area of the handle (where rod cutting force is applied) is narrow, having substantially no width on the inner side of the fold of the handle.

In another known rod cutter, having a pivotable handle, the handle is deformed with an offset to accommodate a wider hand grip when folded. However, the offset handle position is uncomfortable for a user and is necessarily outside the plane of rotary motion of the handle when used for cutting a rod. Further, such a pivotable handle has been the cause of a pinched finger or hand while setting up for use.

It would be desirable to have a compact, manually operated surgical rod cutting device that has an extensible handle for increased rod cutting leverage without any pivotal action to extend the handle. Further, it would be desirable to have the handle entirely within the plane of rotary motion during the rod cutting process. Additionally, it would also be desirable to have the handle configured in such a way that there is less potential for damage to an operator's hand when performing the cutting operation. Moreover, a rod cutter for surgical steel rods should be of a size that permits ready sterilization of the unit as a whole, as well as individual parts of the unit.

SUMMARY OF THE INVENTION

The present invention provides a rod cutter device, preferably designed to set upon a table, wherein the rod cutter provides a relatively easy, manual cutting motion capable of cutting toughened surgical steel rods to produce a burr-free end of the severed rod. The rod cutter includes a rod cutting tool head having first and second rod receiving components. The rod receiving components are rotatable relative to one another on a common horizontal axis and each of the rod receiving components has one or more bore holes therethrough. In a first orientation of the rod receiving components, the bore holes are aligned so that a rod may be slidably received through the aligned bores in each of the rod receiving components, and in a second orientation the bores are misaligned thereby causing a rod traversing a bore in both components to be sheared or cut. In accomplishing such rod cutting, the present invention relies upon a rotary action from a manually operated handle for providing the force needed to misalign the bore holes and thereby sever a rod previously inserted through an aligned pair of bore holes within the first and second rod receiving components.

The handle of the present invention is such that it is extendable thereby allowing an operator to apply greater rod cutting leverage when the handle is extended and also allowing the rod cutter to be substantially more compact when the handle is retracted. Furthermore, an important aspect of the present invention is that an operator may extend the handle using substantially linear motion along a longitudinal axis of the handle wherein portions of the handle slide or telescope with respect to one another when extended and/or retracted. Thus, since there is no folding of the handle, it is an aspect of the present invention that a grip on the free end of the handle may be shaped as desired for distributing the manual rod cutting forces over a wider portion of an operator's hands and still have the handle be substantially vertically straight. In particular, the handle need not be curved in a horizontal direction to accommodate the handle grip when the handle is retracted. Therefore, when cutting a rod the present invention is subject to fewer stresses out of the vertical plane of handle rotation and, additionally, the handle grip may be modified as desired for operator comfort. In fact, a handle grip substantially perpendicular to the length of the handle may be provided without additional cutter modifications.

It is a further aspect of the present invention that it is configured so that at the termination of a rod cutting action wherein the operator's hands are forcefully moving toward the surface upon which the rod cutter is placed, that the nearest distance of the grip from the surface is still far enough from the surface so that the operator's hands do not hit the table. This aspect of the invention is preferably provided by incorporating a handle stop that limits the travel of the handle toward the table. However, in order to insure that rods are cut effectively, it may be the case that the vertical arc the handle is required to travel through during rod cutting is such that a simple raising of the stop to offset the handle grip from the table causes an operator, upon commencing to cut a rod, to either apply force to the grip in an awkward direction (namely somewhat upward) or some of the force expended is wasted since it is not in a direction to expedite cutting of the rod. Therefore, it is a further aspect of the present invention that the handle preferably be provided with a slight bend or bow in the handle in the vertical direction so that upon termination of a cutting action the handle is concave downward with a lowest point occurring between the cutting tool head and the grip, and more preferably closer to the cutting tool than the grip. Furthermore, this configuration of the handle also means that the starting position at the handle is almost vertical to the cutting head. Thus, the force required to make the handle arc to cut the rod is a pulling action toward the operator providing better leverage than a force pressing down.

A further aspect of the present invention relates to a method for cutting surgical rods of a plurality of diameters by inserting a determined surgical rod into an appropriately sized rod receiving bore hole in a tool head, having a plurality of such rod receiving bore holes, wherein the tool head includes at least first and second rod receiving components that are moveable relative to one another so that in a first position the rod can be inserted and in a second position the rod is severed.

A handle means is provided, attached to the first rod receiving component, the handle means capable of moving the first component between the first and second positions. The handle means includes a first handle portion having a first length with one end of the length attached to the first rod receiving component, and a second handle portion having a second length with one end of the second length having a grip. The first and second handle portions are slidably connected between a retracted handle position and an extended handle position. The handle means is rotated through an arc to move the first and second rod receiving components from the first position to the second position in order to sever the rod.

Other features and benefits of the present invention will become apparent from the detailed description with the accompanying figures contained hereinafter.

DETAILED DESCRIPTION

Figure 1:
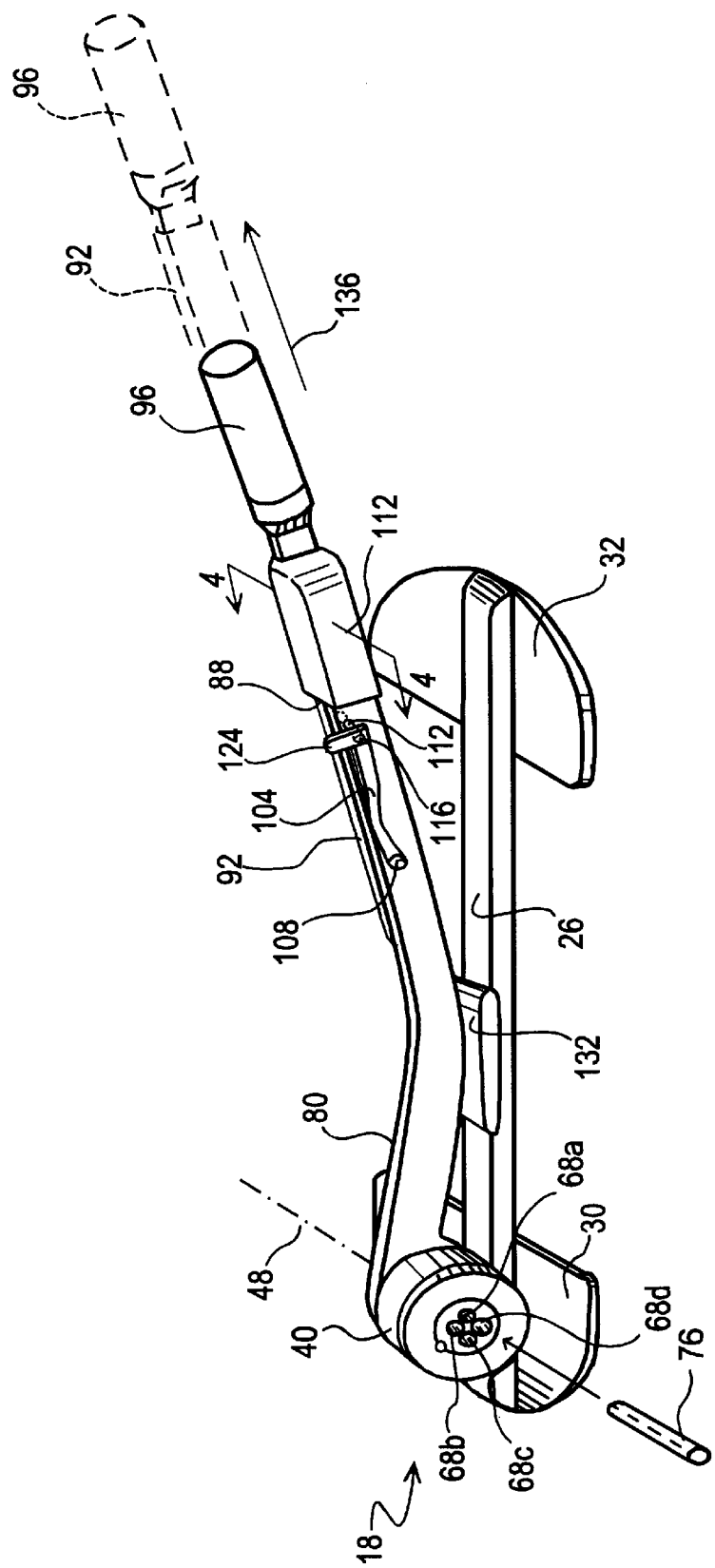
FIG. 1 is a side elevational view of the rod cutter invention.
Figure 2:
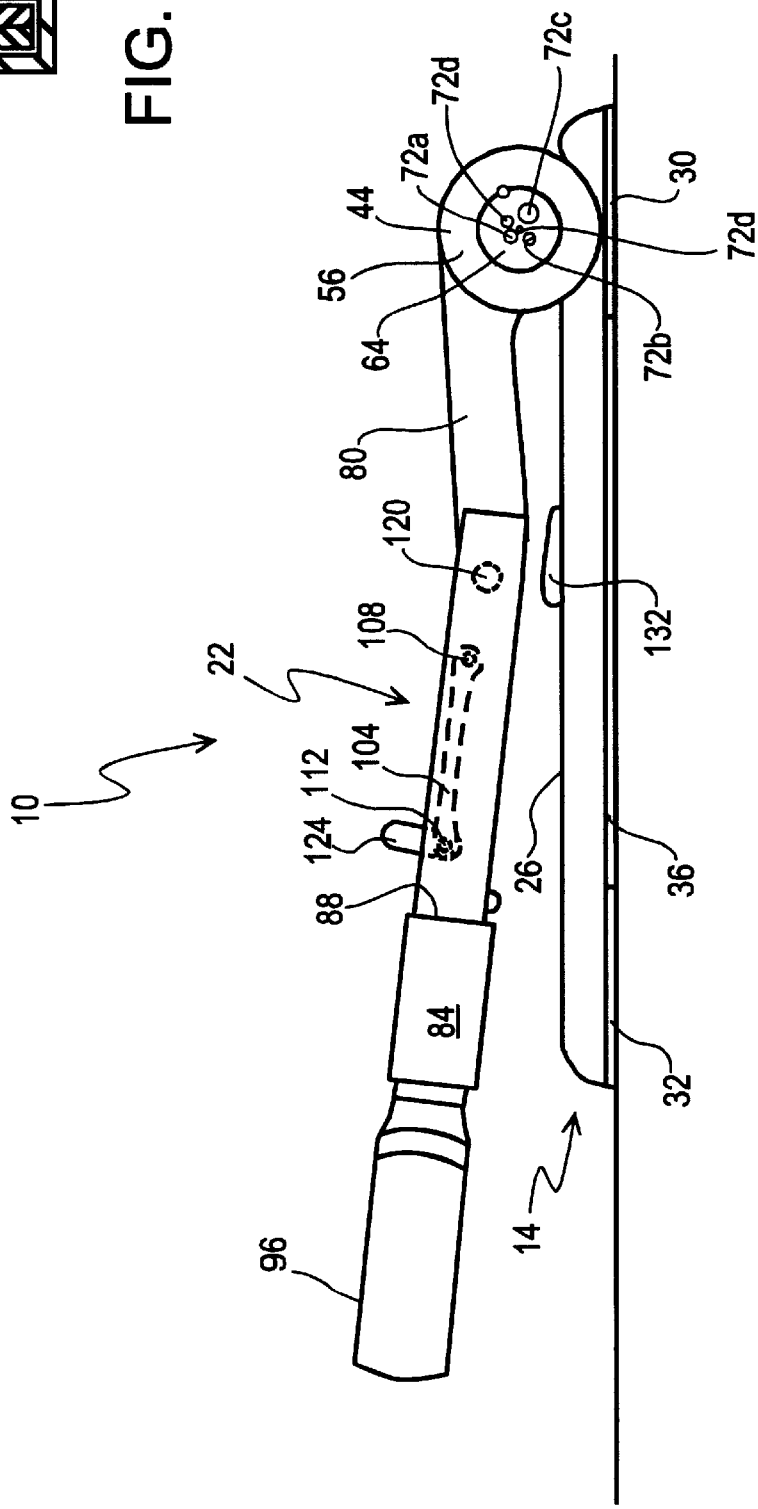
FIG. 2 is a top plan view of the rod cutter invention.
Figure 3:
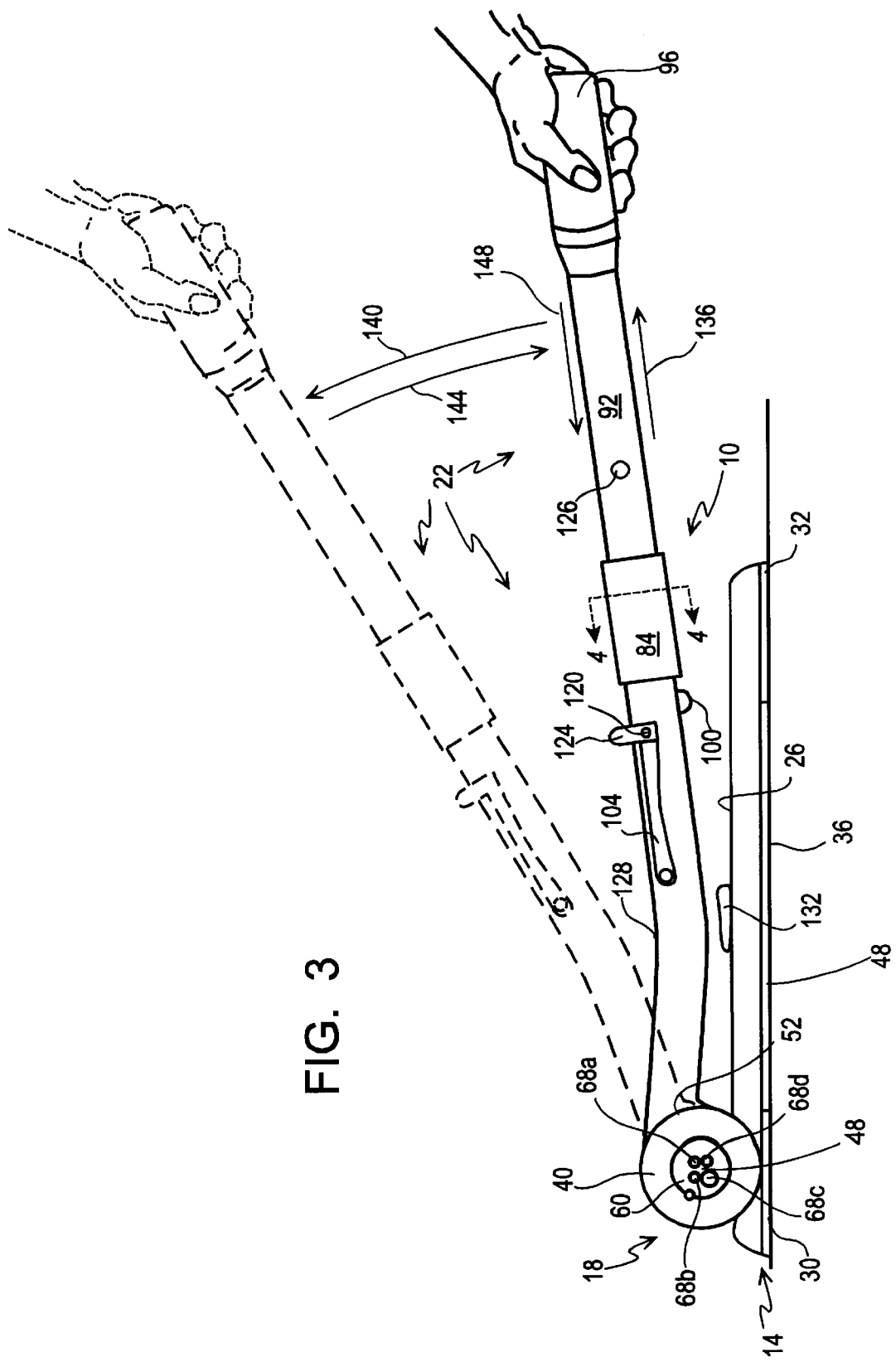
FIG. 3 is an enlarged side elevational view of the cutting head, partially broken away to show internal construction.

FIGS. 1–3 provide various views of the rod cutter 10 of the present invention, these views being referred to interchangeably. As illustrated in these figures, rod cutter 10 may be viewed as including three cooperating functional units, namely a supporting base 14, a rod cutting tool head 18 and a handle 22 (shown in FIGS. 1, 2 and 3 in substantially a horizontal position with the exception of the dashed portion of FIG. 3). The supporting base 14 includes a longitudinal support bar 26 which is attached at its longitudinal end points to lateral stabilizing plates 30, 32 that stabilize the rod cutter 10 upon a surface 36 such as a table by contacting a sufficient amount of the surface 36 laterally to the sides of longitudinal support bar 26 so that there is little opportunity for unintentional non-vertical forces applied to the rod cutter 10 during a cutting operation to cause the rod cutter 10 to tip over. Attached to one end of the supporting base 14 is the rod cutting tool head 18. As best shown in FIG. 1, the rod cutting tool head 18 includes two cylindrical adjacent rod cutting components 40, 44 each aligned with their centers coincident with the axis 48. As best shown in FIGS. 2 and 3, rod cutting components 40, 44 have an outer casing 52, 56, respectively, wherein outer casing 52 is integrally attached to handle 22 and outer casing 56 is fixably attached to longitudinal support bar 26. Additionally, each of the rod cutting components 40, 44 also include a rod shearing subassembly 60, 64, respectively. Note that each such rod shearing subassembly is provided with a plurality of bore holes 68a–68d (FIG. 3) in rod shearing subassembly 60 and 72a–72d (FIG. 2) in rod shearing subassembly 64. These bore holes are used for receiving toughened surgical steel rods as illustrated by the arrows in FIG. 1. Further note that: (a) each of the bore holes 68a–68d is of a different size for accommodating a different gauge of rod; (b) bore hole 72a has the same diameter as bore hole 68a, bore hole 72b has the same diameter as bore hole 68b, and bore hole 72c has the same diameter as bore hole 68c, and bore hole 72d has the same diameter as bore hole 68d; (c) the entire rod cutting component 44, including bore holes 72a–72d, pivots about axis 48 so that when the handle 22 is in an upright position (i.e., substantially vertical position), the bore hole pairs (68a, 72a), (68b, 72b), (68c, 72c) and (68d, 72d) are aligned so that a rod 76 may be received through any one of the pairs; and (d) the bore hole pairs are substantially misaligned when the handle 22 is in its prone or substantially horizontal position.

Figure 4:
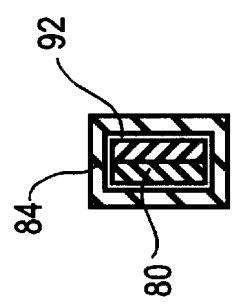
FIG. 4 shows the handle sheath of the present invention.

Regarding the handle 22, as mentioned above, it is integrally attached to rod cutting component 44. Proceeding away from rod cutting component 44 along the length of handle 22 there is a primary handle bar 80 that extends away from the rod cutting tool head 18, wherein its opposite end is integrally attached to a sheath 84. That is, the side of the sheath 84 as shown in FIG. 2 is preferably integral with an end portion of primary handle bar 80 so that a sheath opening 88 (FIG. 4) is adjacent to primary handle bar 80 and such that the sheath opening 88 is a rectangular slot running parallel to primary handle bar 80 and open at both ends. Slidably received in sheath opening 88 is the handle extension 92. Note that the handle extension 92 is preferably substantially parallel to the primary handle bar 80. Further note that when handle extension 92 is in a retracted position wherein substantially all of the handle position is adjacent to the primary handle bar 80, the handle grip 96 is adjacent to one end of the sheath 84. Alternatively, when the handle extension 92 is extended, a majority of the handle extension is not adjacent to the primary handle bar 80 but instead extends away from rod cutting tool head 18.

The handle extension 92 is prevented from completely leaving the sheath opening 88 by a knob or projection 100 extending outwardly, and preferably downwardly, from a side of the handle extension, preferably the bottom most side of the handle. This projection 100 is of sufficient size so that it cannot enter the sheath opening 88. A second mechanism for retaining handle extension 92 in place is provided by a spring latch 104 that is attached to primary handle bar 80. A fastener such as a screw or rivet 108 may be used to permanently connect one end of the latch spring 104 to the handle bar 80. The opposite end of the latch spring 104 carries a latching pin 112 that is urged by the spring in the direction of handle bar 80 and is received within a bore 116 that penetrates through handle bar 80. Thus, the free end of the latching pin 112 is urged against an interior side of handle extension 92 wherein when the handle extension 92 is in a fully extended position, the pin enters a mating recess 120 provided on the surface of handle extension 92 contacting primary handle bar 80. Thus, when the latching pin 112 engages mating recess 120, the handle extension 92 is not only further prevented from being removed from the sheath opening 88 but also is locked in place so that it cannot inadvertently retract. Additionally, note that the spring latch 104 also includes a finger tab 124 which may be used by an operator of the present invention for releasing or extracting the latching pin 112 from the mating recess 120 when an operator desires to retract the handle extension 92. Note that spring latch 104 also engages mating recess 126 for locking the handle in the closed position so that the handle cannot accidentally extend.

Note that whether the handle 22 is retracted or extended, the grip 96 is far enough above the surface 36 so that an operator's hand about the grip 96 is not likely to come in contact with the surface 36. This important feature of the present invention is provided by the bend 128 in primary handle bar 80 in conjunction with the handle stop 132. That is, by positioning the handle stop 132 immediately below the lowest potential point of the primary handle bar 80 (i.e., immediately below the bend 128), the remaining portion of the primary handle bar 80 extending from the bend 128 away from the tool head 18 is angled upwardly at a sufficient rate to provide a safe distance between the surface 36 and an operator's hand about the grip 96 and still at the same time provide sufficient rotational angle to effectively shear a rod 76.

Further note that all exterior surfaces of the rod cutter 10 may be grained thereby allowing the rod cutter to be more easily gripped with potentially wet and/or slick gloved hands. Additionally, it is preferable that the surface 36 contacting portions of the plates 30 and 32 are cross-grained so that the rod cutter 10 is resistant to sliding on, for example, a cloth covered table for surface 36.

In operation, once the rod cutter 10 has been placed upon surface 36 as shown in the figures, depending on the gauge of a surgical rod to be cut and the strength of the operator, the handle 22 either remains retracted or is extended. The present invention can therefore be used in a retracted position for the cutting of thinner rods, in contrast to prior art designs which only permit operation once the handle is in a rotationally, fully extended position. To extend the handle 22, the operator merely pulls the grip 96 in the direction of arrow 136. The pulling motion causes handle extension 92 to slide in sheath opening 88 away from tool head 18 until the projection 100 comes in contact with an outside edge of sheath 84 as shown in FIG. 3. Concomitantly with this contact, latching pin 112 enters mating recess 120 to lock the handle extension 92 into place so that it can neither extend nor retract inadvertently. Subsequently, the operator rotates the handle 22 in the direction of arrow 140 about axis 48 (FIG. 3) until the handle 22 is in a substantially vertical position (i.e., handle extension 92 is substantially vertical). In this position, each of the bore hole pairs in the tool head 18 are in alignment. The operator may then insert the rod 76 into an appropriately sized bore hole pair 68, 72 so that the location of the cut to be made on rod 76 is positioned between the rod cutting components 40, 44 and subsequently the operator rotates the handle 22 in the direction of arrow 144 thereby causing the rod 76 to be sheared off at the desired position by the time the handle 22 contacts the handle stop 132. Following this, the severed portions of bars 76 may be removed and the operator may apply finger pressure to finger tab 124 to disengage latching pin 112 from mating recess 120 and, once disengaged, the handle extension 92 can be slid in the direction of direction arrow 148 (FIG. 3) into the sheath 84 so that the rod cutter 10 may return to its initial compact configuration.

Variations on the above-described rod cutter 10 are also contemplated by the present invention. In particular, one skilled in the art will readily appreciate that instead of a combination of the sheath 84 and the handle extension 92 for extending the handle 22, the primary handle bar 80 could be of a telescoping configuration wherein the handle extension 92 is slidable within a recess internal to primary handle bar 80 and extending along its length from its free end toward the rod cutting tool 18. In another alternative embodiment, there may be no bend 128 in the primary handle bar 80. Instead, the primary handle bar 80 may be smoothly curved so that in the prone position it is downwardly convex when viewed from the side as in FIG. 2. Alternatively, to protect a user's hand from injury, an elevated stop (not shown) can be used to prevent rotary movement beyond a desired height of the handle from the table; however, the handle must still be able to move so that proper insertion of a rod can occur and must allow for rotation into a cutting position.

The foregoing discussion of the invention has been presented for purposes of illustration and description. Further, the description is not intended to limit the invention to the form disclosed herein. Consequently, variation and modification commensurate with the above teachings, within the skill and knowledge of the relevant art, are within the scope of the present invention. The embodiment described hereinabove is further intended to explain the best mode presently known of practicing the invention and to enable others skilled in the art to utilize the invention as such, or in other embodiments, and with the various modifications required by their particular applications or uses of the invention. It is intended that the appended claims be construed to include alternative embodiments to the extent permitted by the prior art.

What is claimed is:

1. A method for cutting surgical rods, comprising:

inserting a surgical rod into a tool head, said tool head having at least first and second rod receiving components that are moveable relative to one another so that in a first position the rod is inserted and in a second position the rod is severed;

providing a handle means attached to said first rod receiving component, said handle means capable of moving said first component between said first and second positions, said handle means including a first handle portion having a first length with one end of the length attached to said first rod receiving component and a second handle portion having a second length with one end of said second length having a grip, wherein at least one of said first and second handle portions has a bend for preventing a user's hand on said grip from contacting the surface when cutting the rod, said first and second handle portions being slidably connected between a retracted handle position and an extended handle position by a sheath attached to one of said first and second handle portions, said sheath having a passageway in which one of said first and second handle portions slides, said passageway maintaining said first and second lengths in parallel alignment, said handle means including a stopping means for prohibiting said second handle portion slidable within said sheath from disengaging from said sheath, said stopping means having a projection on one of said first and second lengths, said projection being transverse to said length having said projection; and rotating said handle means through an arc to move said first and second rod receiving components from said first position to said second position in order to sever said rod, said handle contacting an elevated stop that supports said handle means above the underlying surface, said elevated stop being positioned beneath said bend.

2. A surgical rod cutter, comprising:

a base means for supporting said rod cutter on an underlying surface;

a tool head means for shearing a rod, said tool head means carried by said base means, said tool head means having at least first and second rod receiving components that are moveable relative to one another so that in a first position the rod is inserted and in a second position the rod is cut, said first and second rod receiving components including, respectively, a first and second plurality of rod receiving bores for receiving different sized rods;

a handle means directly attached to said first rod receiving component for moving said first component between said first and second positions, said handle means having a bend therein;

an elevated stop operatively connected to said base means to prevent rotary movement beyond a desired height of said handle means from the underlying surface and to support said handle means above the underlying surface when said tool head means is in said second position, said elevated stop being positioned immediately below said bend in said handle means.

3. A rod cutter, comprising:

a base means for supporting said rod cutter on an underlying surface;

a tool head means for shearing a rod, said tool head means carried by said base means, said tool head means having at least first and second rod receiving components that are moveable relative to one another so that in a first position the rod is inserted and in a second position the rod is cut, said first and second rod receiving components including, respectively, a first and second plurality of rod receiving bores for receiving different sized rods;

a handle means directly attached to said first rod receiving component for moving said first component between said first and second positions;

wherein said handle means includes:
  (a) a first handle portion having a first length with one end of the length attached to said first rod receiving component;
  (b) a second handle portion having a second length with one end of said second length having a grip, wherein at least one of said first and second handle portions has a bend for preventing a user's hand on said grip from contacting the surface when cutting the rod;
  (c) connection means for slidably connecting said first and second handle portions, said connection means having an interior wherein at least one of said first and second handle portions is slidable therein between a retracted handle position and an extended handle position, said extended position displacing said grip further from said tool head means than said retracted position so that greater leverage is exerted on said grip when cutting said rod, said connection means including a sheath attached to one of said first and second handle portions, said sheath having a passageway in which one of said first and second handle portions slides, said passageway maintaining said first and second lengths in parallel alignment wherein said first and second lengths are slidable relative to one another;

a stopping means for prohibiting said handle portion slidable within said sheath from disengaging from said sheath, said stopping means including a projection on one of said first and second lengths, said projection being traverse to said length having said projection; and an elevated stop operatively connected to said base means to prevent rotary movement beyond a desired height of said handle means from the underlying surface and to support said handle means a distance above the underlying surface when said tool head means is in said second position, said elevated stop being positioned beneath said bend.

4. A rod cutter, as claimed in claim 3, wherein said handle means extends by applying a force to said grip along said second length.

5. A rod cutter, as claimed in claim 3, wherein said handle means retracts from said extended position by applying a force to said grip along said second length and toward said tool head.

6. A rod cutter, as claimed in claim 3, wherein said first and second handle portions are prohibited from pivoting with respect to each other.

7. A rod cutter, as claimed in claim 3, wherein said first and second handle portions are in telescoping relationship to one another.

8. A rod cutter, as claimed in claim 3, wherein said handle grip moves rotationally.

* * * * *